United States Patent
Lands et al.

(10) Patent No.: US 6,451,018 B1
(45) Date of Patent: *Sep. 17, 2002

(54) LAPAROSCOPIC BIPOLAR ELECTROSURGICAL INSTRUMENT

(75) Inventors: Michael John Lands, Clearwater, FL (US); Stephen Wade Lukianow, Boulder, CO (US); Donald Robert Loeffler, Louisville, CO (US); James Steven Cunnigham, Boulder, CO (US); Kate Ryland Lawes, Superior, CO (US); Daniel Lee Trimberger, II, Greeley, CO (US); Mathew Erle Mitchell; Jenifer Serafin Kennedy, both of Boulder, CO (US)

(73) Assignee: Sherwood Services AG, Schaffhausen (CH)

( * ) Notice: Subject to any disclaimer, the term of this patent is extended or adjusted under 35 U.S.C. 154(b) by 100 days.

This patent is subject to a terminal disclaimer.

(21) Appl. No.: 09/591,330

(22) Filed: Jun. 9, 2000

Related U.S. Application Data

(63) Continuation of application No. 08/970,472, filed on Nov. 14, 1997, now Pat. No. 6,228,083.

(51) Int. Cl.$^7$ .............................................. A61B 18/14
(52) U.S. Cl. ............................ 606/50; 606/46; 606/48; 606/207; 606/208
(58) Field of Search .............................. 606/46, 48–52, 606/170, 207, 208

(56) References Cited

U.S. PATENT DOCUMENTS

| | | |
|---|---|---|
| 371,664 A | 10/1887 | Brannan et al. |
| 702,472 A | 6/1902 | Pignolet |
| 728,883 A | 5/1903 | Downes |
| 1,586,645 A | 6/1926 | Bierman |

(List continued on next page.)

FOREIGN PATENT DOCUMENTS

| | | |
|---|---|---|
| CA | 2104423 | 2/1994 |
| EP | 0 518 230 A1 | 12/1992 |
| EP | 0 584 787 A1 | 3/1994 |
| EP | 0 853 922 A1 | 7/1998 |
| SU | 401367 | 11/1974 |

OTHER PUBLICATIONS

Bergdah Et Al., Studies on Coagulation and the Development of an Automatic Computerized Bipolar Coagulator, J. Neurosurg. vol. 75, Jul. 1991 pp 148–151.

Sigel Et Al., The Mechanism of Blood Vessel Closure by High Frequency Electrocoagulation, Surgery & Gynecology and Obstetrics, Oct. 1965 pp. 823–831.

*Primary Examiner*—Lee Cohen

(57) ABSTRACT

A laparoscopic bipolar electrosurgical instrument can apply a large closure force between its jaws without damaging the small yoke assembly. The instrument comprises: a first jaw having a first flange with a first slot, and a second jaw having a second flange with a second slot, wherein the first and second jaws are located at a distal end of the instrument and comprise an electrically conductive material for conducting bipolar electrosurgical current therebetween; a yoke attached to a pushrod and positioned to electrically insulate the first flange from the second flange, the yoke having a first side facing the first flange and a second side facing the second flange, the yoke further comprising a first shoulder and a second shoulder; a first pin located on the first side and movably engaged with the first slot; a second pin located on the second side and movably engaged with the second slot; the first slot and the second slot shaped such that an angle, subtended by the first and second jaws, decreases with distal motion of the pushrod, and first and second cul-de-sacs positioned respectively in the first and second slots to relieve shear stresses on the first and second pins approximately when the first and second shoulders respectively engage the first and second flanges to provide a closure force between the first and second jaws.

8 Claims, 5 Drawing Sheets

U.S. PATENT DOCUMENTS

| | | |
|---|---|---|
| 2,002,594 A | 5/1935 | Wappler et al. |
| 2,176,479 A | 10/1939 | Willis |
| 3,643,663 A | 2/1972 | Sutter |
| 3,651,811 A | 3/1972 | Hildebrandt et al. |
| 3,920,021 A | 11/1975 | Hiltebrandt |
| 3,938,527 A | 2/1976 | Rioux |
| 3,952,749 A | 4/1976 | Fridolph et al. |
| 4,005,714 A | 2/1977 | Hiltebrandt |
| 4,370,980 A | 2/1983 | Lottick |
| 4,552,143 A | 11/1985 | Lottick |
| 4,597,379 A | 7/1986 | Kihn et al. |
| 4,671,274 A | 6/1987 | Sorochenko |
| 4,685,459 A | 8/1987 | Koch et al. |
| 4,763,669 A | 8/1988 | Jaeger |
| 4,887,612 A | 12/1989 | Esser et al. |
| 4,938,761 A | 7/1990 | Ensslin |
| 5,007,908 A | 4/1991 | Rydell |
| 5,026,370 A | 6/1991 | Lottick |
| 5,116,332 A | 5/1992 | Lottick |
| 5,151,102 A | 9/1992 | Kamiyama et al. |
| 5,197,964 A | 3/1993 | Parins |
| 5,215,101 A | 6/1993 | Jacobs et al. |
| 5,217,458 A | 6/1993 | Parins |
| 5,250,047 A | 10/1993 | Rydell |
| 5,258,006 A | 11/1993 | Rydell et al. |
| 5,277,201 A | 1/1994 | Stern |
| 5,282,799 A | 2/1994 | Rydell |
| 5,290,286 A | 3/1994 | Parins |
| 5,318,589 A | 6/1994 | Lichtman |
| 5,324,289 A | 6/1994 | Eggers |
| 5,330,471 A | 7/1994 | Eggers |
| 5,334,215 A | 8/1994 | Chen |
| 5,342,359 A | 8/1994 | Rydell |
| 5,342,381 A | 8/1994 | Tidemand |
| 5,352,222 A | 10/1994 | Rydell |
| 5,356,408 A | 10/1994 | Rydell |
| 5,389,098 A | 2/1995 | Tsuruta et al. |
| 5,389,104 A | 2/1995 | Hahnen et al. |
| 5,391,166 A | 2/1995 | Eggers |
| 5,403,312 A | 4/1995 | Yates et al. |
| 5,411,519 A | 5/1995 | Tovey et al. |
| 5,431,674 A | 7/1995 | Basile et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell |
| 5,445,658 A | 8/1995 | Durrfeld et al. |
| 5,456,684 A | 10/1995 | Schmidt et al. |
| 5,462,546 A | 10/1995 | Rydell |
| 5,472,443 A | 12/1995 | Cordis et al. |
| 5,478,351 A | 12/1995 | Meade et al. |
| 5,484,436 A | 1/1996 | Eggers et al. |
| 5,509,922 A * | 4/1996 | Aranyl et al. .................. 606/46 |
| 5,514,134 A | 5/1996 | Rydell et al. |
| 5,527,313 A | 6/1996 | Scott et al. |
| 5,531,744 A | 7/1996 | Nardella et al. |
| 5,540,684 A | 7/1996 | Hassler, Jr. |
| 5,540,685 A | 7/1996 | Parins et al. |
| 5,558,672 A | 9/1996 | Edwards et al. |
| 5,569,241 A | 10/1996 | Edwards |
| 5,573,535 A | 11/1996 | Viklund |
| 5,603,711 A | 2/1997 | Parins et al. |
| 5,603,723 A | 2/1997 | Aranyi et al. |
| 5,626,578 A | 5/1997 | Tihon |
| 5,637,110 A * | 6/1997 | Pennybacker et al. ......... 606/52 |
| 5,658,281 A | 8/1997 | Heard |
| 5,667,526 A | 9/1997 | Levin |
| 5,674,220 A | 10/1997 | Fox et al. |
| 5,693,051 A | 12/1997 | Schulze et al. |
| 5,700,261 A | 12/1997 | Brinkerhoff |
| 5,702,390 A | 12/1997 | Austin et al. |
| 5,707,369 A | 1/1998 | Vaitekunas et al. |
| 5,743,906 A | 4/1998 | Parins et al. |
| 5,766,166 A | 6/1998 | Hooven |
| 5,766,170 A | 6/1998 | Eggers |
| 5,769,849 A | 6/1998 | Eggers |
| 5,776,128 A | 7/1998 | Eggers |
| 5,776,130 A | 7/1998 | Buysse et al. |
| 5,792,137 A | 8/1998 | Carr et al. |
| 5,800,449 A | 9/1998 | Wales |
| 5,810,808 A | 9/1998 | Eggers |
| 5,814,043 A | 9/1998 | Shapeton |
| 5,827,279 A | 10/1998 | Hughett et al. |
| 5,827,281 A | 10/1998 | Levin |
| 5,843,080 A | 12/1998 | Fleenor et al. |
| 5,849,022 A * | 12/1998 | Sakashita et al. .............. 606/51 |
| 5,891,141 A | 4/1999 | Rydell |
| 5,891,142 A | 4/1999 | Eggers et al. |
| 5,902,301 A | 5/1999 | Olig |
| 5,908,420 A | 6/1999 | Parins et al. |
| 5,913,874 A | 6/1999 | Berns et al. |
| 5,921,984 A | 7/1999 | Sutcu et al. |
| 5,935,126 A | 8/1999 | Riza |
| 5,951,549 A | 9/1999 | Richardson et al. |
| 5,954,720 A | 9/1999 | Wilson et al. |
| 5,976,132 A * | 11/1999 | Morris ........................ 606/50 |
| 6,004,335 A | 12/1999 | Viatekunas et al. |
| 6,039,733 A | 3/2000 | Buysse et al. |
| 6,050,996 A | 4/2000 | Schmaltz et al. |
| 6,053,914 A | 4/2000 | Eggers et al. |
| RE36,795 E | 7/2000 | Rydell |
| 6,083,223 A | 7/2000 | Baker |
| 6,086,586 A | 7/2000 | Hooven |
| 6,090,107 A | 7/2000 | Borgmeier et al. |
| 6,099,550 A | 8/2000 | Yoon |
| 6,110,171 A | 8/2000 | Rydell |
| 6,113,596 A | 9/2000 | Hooven et al. |
| 6,113,598 A | 9/2000 | Baker |
| 6,126,658 A | 10/2000 | Baker |
| 6,152,923 A | 11/2000 | Ryan |
| 6,174,309 B1 | 1/2001 | Wrublewski et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,206,877 B1 | 3/2001 | Kese et al. |
| 6,228,083 B1 * | 5/2001 | Lands et al. ................... 606/46 |
| 6,334,861 B1 * | 1/2002 | Chandler et al. .............. 606/50 |

* cited by examiner

FIG_2

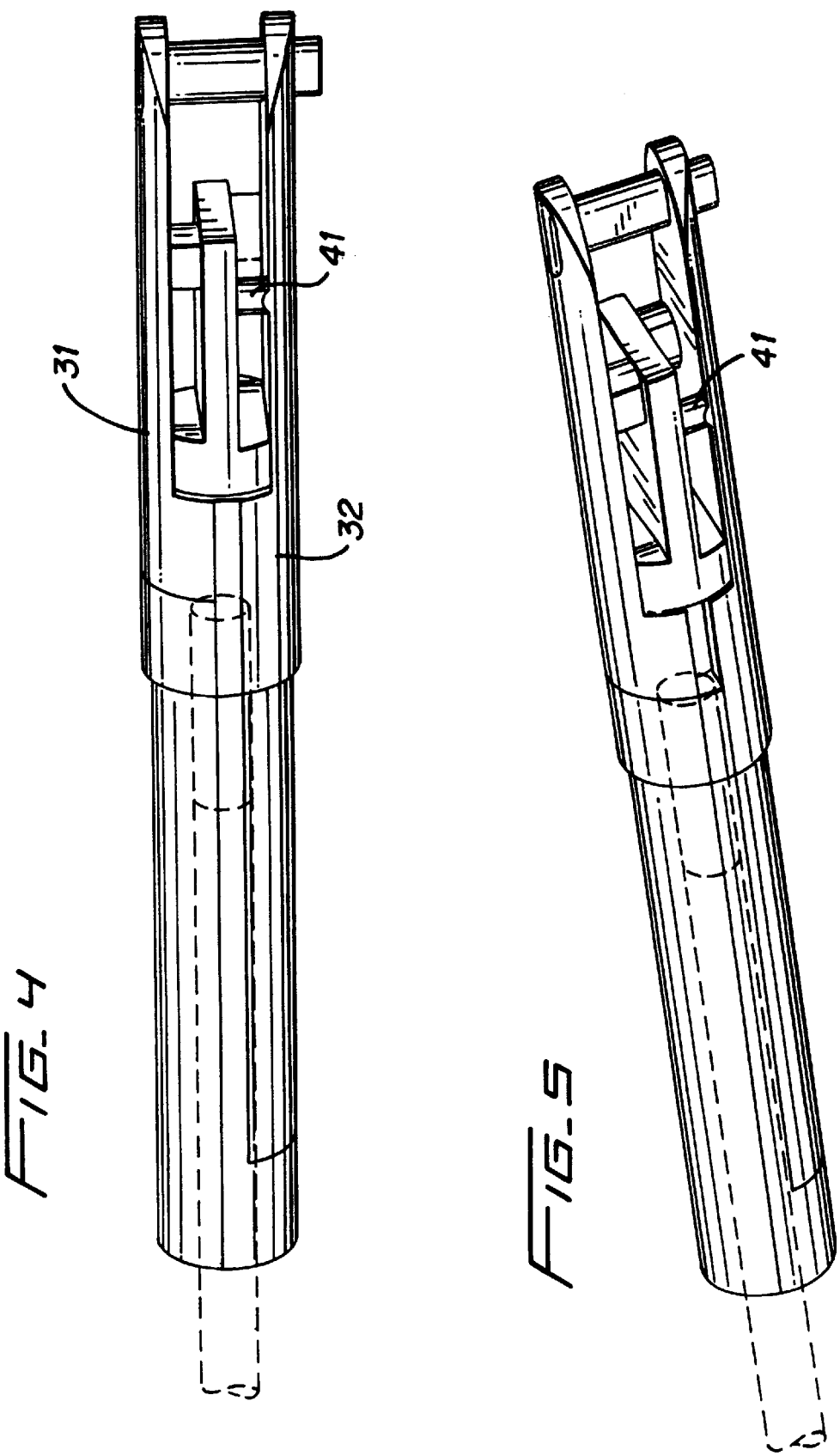

LAPAROSCOPIC BIPOLAR ELECTROSURGICAL INSTRUMENT

This application is a continuation of U.S. application Ser. No. 08/970,472 filed on Nov. 14, 1997, now U.S. Pat. No. 6,228,083.

FIELD OF THE INVENTION

This relates to an electrosurgical instrument for performing laparoscopic surgical procedures, and more particularly to a laparoscopic electrosurgical instrument that is capable of grasping vessels and vascular tissue with sufficient force between two bipolar jaws to seal the vessel or vascular tissue.

BACKGROUND OF THE DISCLOSURE

Laparoscopic surgical instruments are used to perform surgical operation without making large incisions in the patient. The laparoscopic instruments are inserted into the patient through a cannula, or port, that has been made with a trocar. Typical sizes for cannulas range from three millimeters to twelve millimeters. Smaller cannulas are usually preferred, and this presents a design challenge to instrument manufacturers who must find ways to make surgical instruments that fit through the cannulas.

Certain surgical procedures require cutting blood vessels or vascular tissue. This sometimes presents a problem for surgeons because it is difficult to suture blood vessels using laparoscopic tools. Very small blood vessels, in the range below two millimeters in diameter, can often be closed using standard electrosurgical techniques. If a larger vessel is severed, it may be necessary for the surgeon to convert the laparoscopic procedure into an open-surgical procedure and thereby abandon the benefits of laparoscopy.

Several journal articles have disclosed methods for sealing small blood vessels using electrosurgery. An article entitled *Studies on Coagulation and the Development of an Automatic Computerized Bipolar Coagulator*, J. Neurosurg., Volume 75, Jul. 1991, describes a bipolar coagulator which is used to seal small blood vessels. The article states that it was not possible to safely coagulate arteries with a diameter larger than 2 to 2.5 mm. A second article is entitled *Automatically Controlled Bipolar Electrocoagulation—"COA-COMP"*, Neurosurg. Rev. (1984), pp. 187–190. This article describes a method for terminating electrosurgical power to the vessel so that charring of the vessel walls can be avoided.

It has been recently determined that electrosurgical methods may be able to seal larger vessels using an appropriate electrosurgical power curve, coupled with an instrument capable of applying a large closure force to the vessel walls. It is thought that the process of coagulating small vessels is fundamentally different than electrosurgical vessel sealing. Coagulation is defined as a process of desiccating tissue wherein the tissue cells are ruptured and dried. Vessel sealing is defined as the process of liquefying the collagen in the tissue so that it crosslinks and reforms into a fused mass. Thus, coagulation of small vessels is sufficient to permanently close them. Larger vessels need to be sealed to assure permanent closure.

It would be desirable to have a surgical tool capable of applying electrosurgical energy, capable of applying a large closure force to the vessel walls, and also capable of fitting through a cannula. A large closure force between the jaws typically requires a large moment about the pivot for each jaw. This presents a challenge because the first and second pins have a small moment arm with respect to the pivot of each jaw. A large force, coupled with a small moment arm, is undesirable because the large forces may shear the first and second pins. It is also undesirable to increase the moment arm of the first and second pins because the physical size of the yoke might not fit through a cannula.

Several bipolar laparoscopic instruments are known. For example, U.S. Pat. No. 3,938,527 discloses a bipolar laparoscopic instrument for tubal cauterization. U.S. Pat. No. 5,250,047 discloses a bipolar laparoscopic instrument with a replaceable electrode tip assembly. U.S. Pat. No. 5,445,638 discloses a bipolar coagulation and cutting forceps with first and second conductors extending from the distal end. U.S. Pat. No. 5,391,166 discloses a bipolar endoscopic instrument having a detachable working end. U.S. Pat. No. 5,342,359 discloses a bipolar coagulation device.

The present invention solves the problem of providing a large closure force between the jaws of a laparoscopic bipolar electrosurgical instrument, using a compact design that fits through a cannula, without risking structural failure of the instrument yoke.

SUMMARY OF THE INVENTION

The present invention is an instrument for applying bipolar electrosurgical current to tissue in a laparoscopic operation with the added benefit of providing a large closure force between the instrument jaws. The large closure force may be particularly useful for vessel sealing operations. An advantage of the present invention is that tissue can be grasped and clamped with a relatively large closure force without damage to the yoke. The yoke is capable of transmitting the large closure force to the instrument jaws while being small enough to fit through a cannula The laparoscopic bipolar electrosurgical instrument comprises first and second jaws having, respectively, first and second flanges with first and second slots. The instrument is electrically connected to an electrosurgical generator, and conducts bipolar electrosurgical current to the first and second jaws. A yoke is attached to a pushrod and positioned to electrically insulate the first flange from the second flange. First and second pins on the yoke are designed to engage the first and second slots, respectively, in a cam-follower arrangement that opens and closes the jaws with linear motion of the yoke. The yoke is preferably a "push yoke" which means that linear motion of the yoke in the direction of the distal end of the instrument will cause the jaws to close together.

The yoke has first and second shoulders that are spaced apart from the first and second flanges until the jaws are in close arcuate proximity to each other. At that point, the first and second shoulders engage the first and second flanges, whereby further distal motion of the yoke applies a force to the first and second flanges that creates a moment about the pivot of each jaw. In general, the cam-follower arrangement of pins and slots may be designed to provide coarse motion of the jaws with relatively small forces. Large closure forces, once the jaws are relatively close together, may be obtained by pressing the shoulders against the flanges. The first and second pins move into cul-de-sacs in the first and second slots to protect them from large shear stresses when the shoulders are applying relatively large forces to the flanges. Thus, the first and second pins may be made from an electrically insulative material that is not designed to handle large shear stresses, large closure forces may be obtained, and the entire assembly may be compact and fit through a cannula A method of making the laparoscopic bipolar electrosurgical instrument is described, comprising the following steps: forming a first jaw having a first flange with a first slot, and a second jaw having a second flange with a second slot; attaching a yoke to a pushrod; electrically insulating the first flange from the second flange with the yoke; engaging first and second pins with the first and second slots; positioning first and second cul-de-sacs respectively in the first and second slots to relieve shear stresses on the first and second pins at a subtended angle approximately wherein first and second shoulders engage the first and second flanges.

BRIEF DESCRIPTION OF THE DRAWINGS

FIG. 4 is perspective view of the distal end of the instrument with the jaws removed.

FIG. 5 is another perspective of FIG. 4.

DETAILED DESCRIPTION OF THE INVENTION

Figure 1:
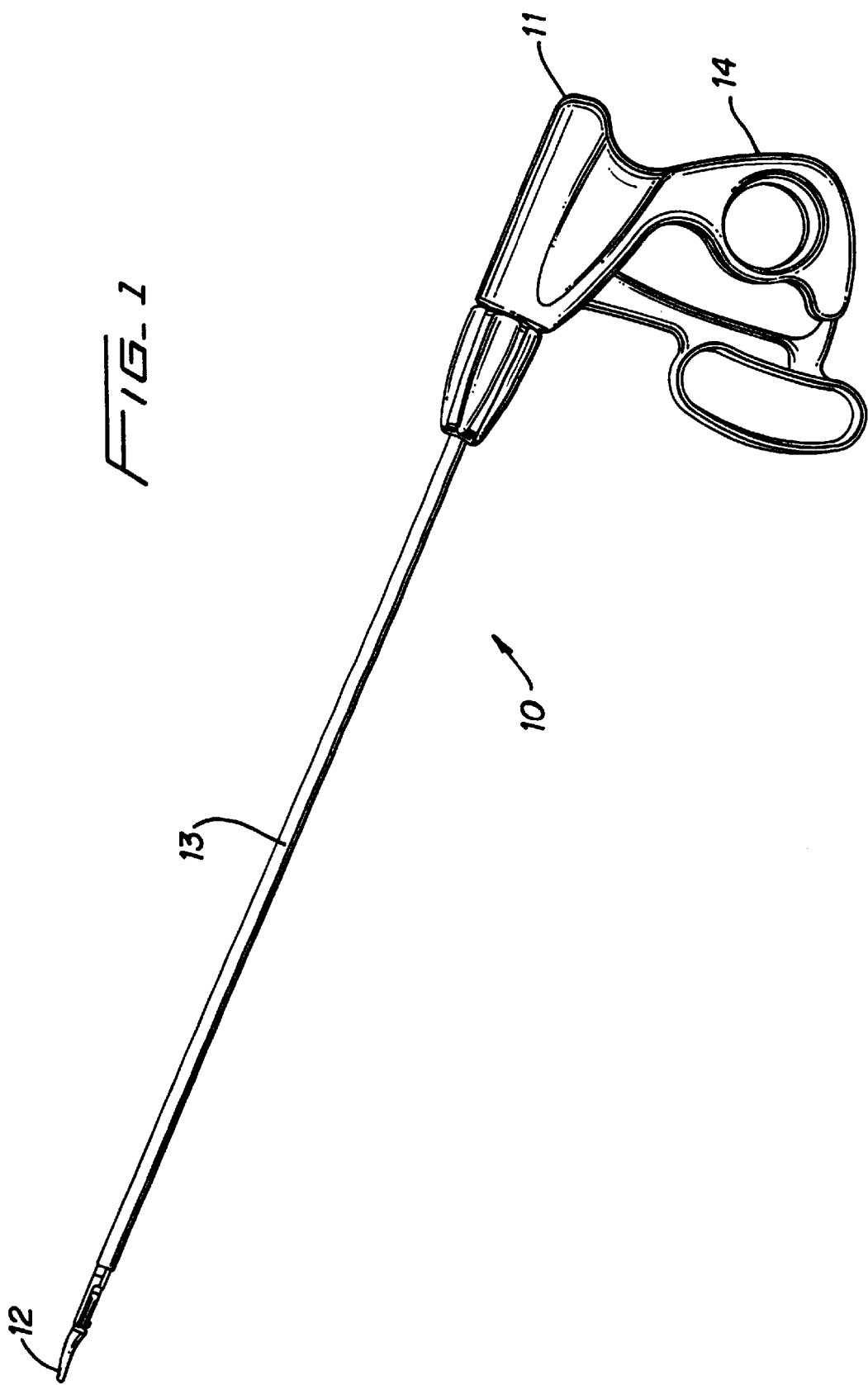
FIG. 1 is a perspective view of a laparoscopic bipolar electrosurgical instrument.

A laparoscopic bipolar electrosurgical instrument 10 is shown in FIG. 1. The instrument 10 has a proximal end 11 with a handle 14 for holding and manipulating the instrument 10. A distal end 12 on the instrument 10 is used for surgical manipulation of tissue. The instrument 10 comprises an elongate tube 13 that is sized to fit through a cannula for laparoscopic operations, and in different embodiments may be sized to fit through either a five or seven millimeter cannula.

Figure 2:
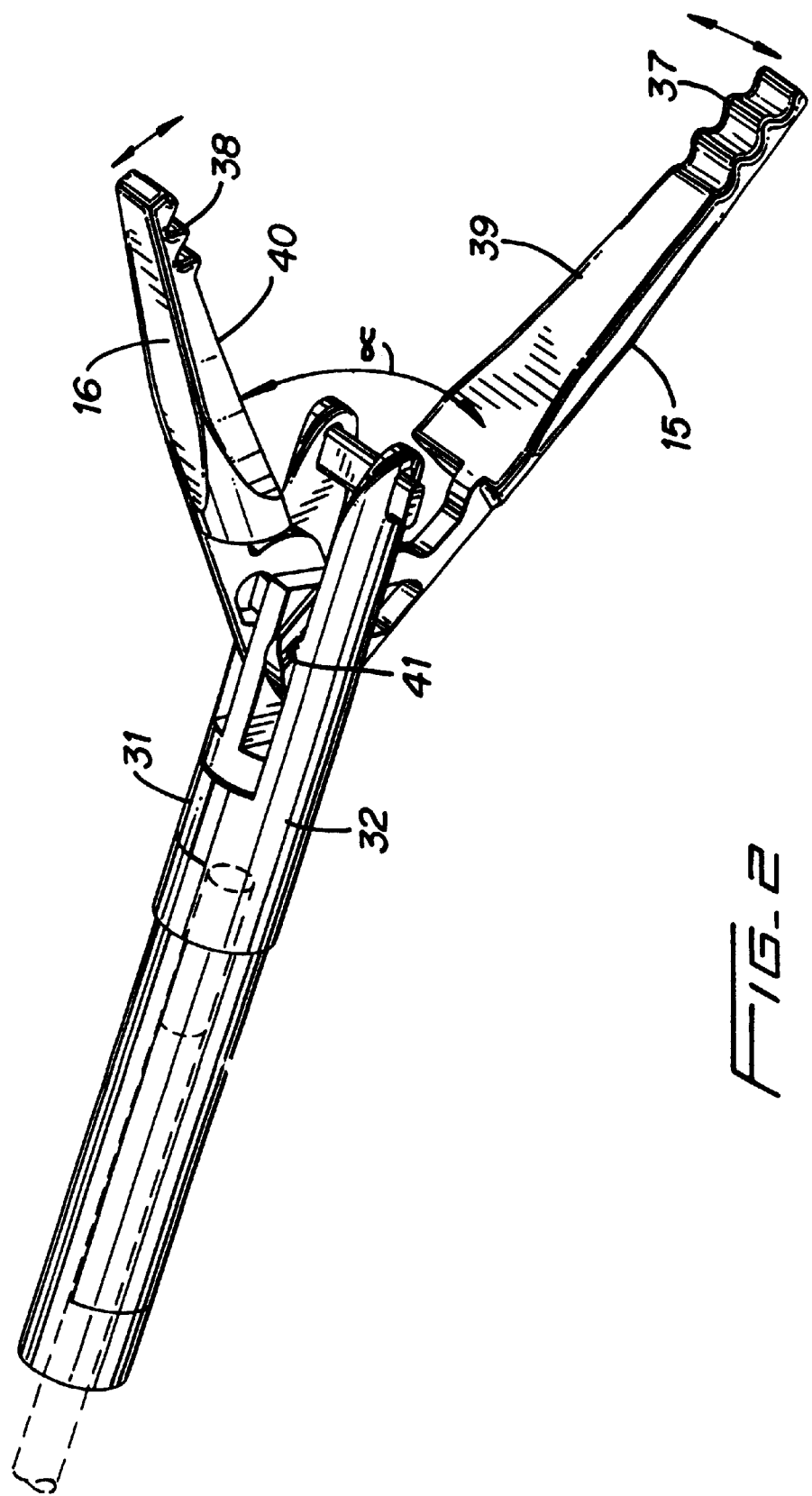
FIG. 2 is a perspective view of the distal end and jaws of the instrument in FIG. 1.

A portion of the distal end 12 of the instrument 10 is shown in FIG. 2. A first jaw 15 and a second jaw 16 are shown in an open position. An angle a is subtended by the jaws 15 and 16. Closing of the jaws 15 and 16 is defined as a reduction of the angle a subtended by the jaws 15 and 16. Similarly, opening of the jaws 15 and 16 is defined as an enlargement of the angle a. The angle a is zero when the jaws 15 and 16 are closed together. The center of rotation for the first jaws 15 is at the first pivot 41, and the center of rotation for the second jaw 16 is at the second pivot 42. The first pivot 41 is located on an outer nose piece 32, and fits in a first pivot hole 43 located on the first flange 18. The second pivot 42 is located on an inner nose piece 31, and fits in a second pivot hole 44 located on the second flange 20.

Figure 3:
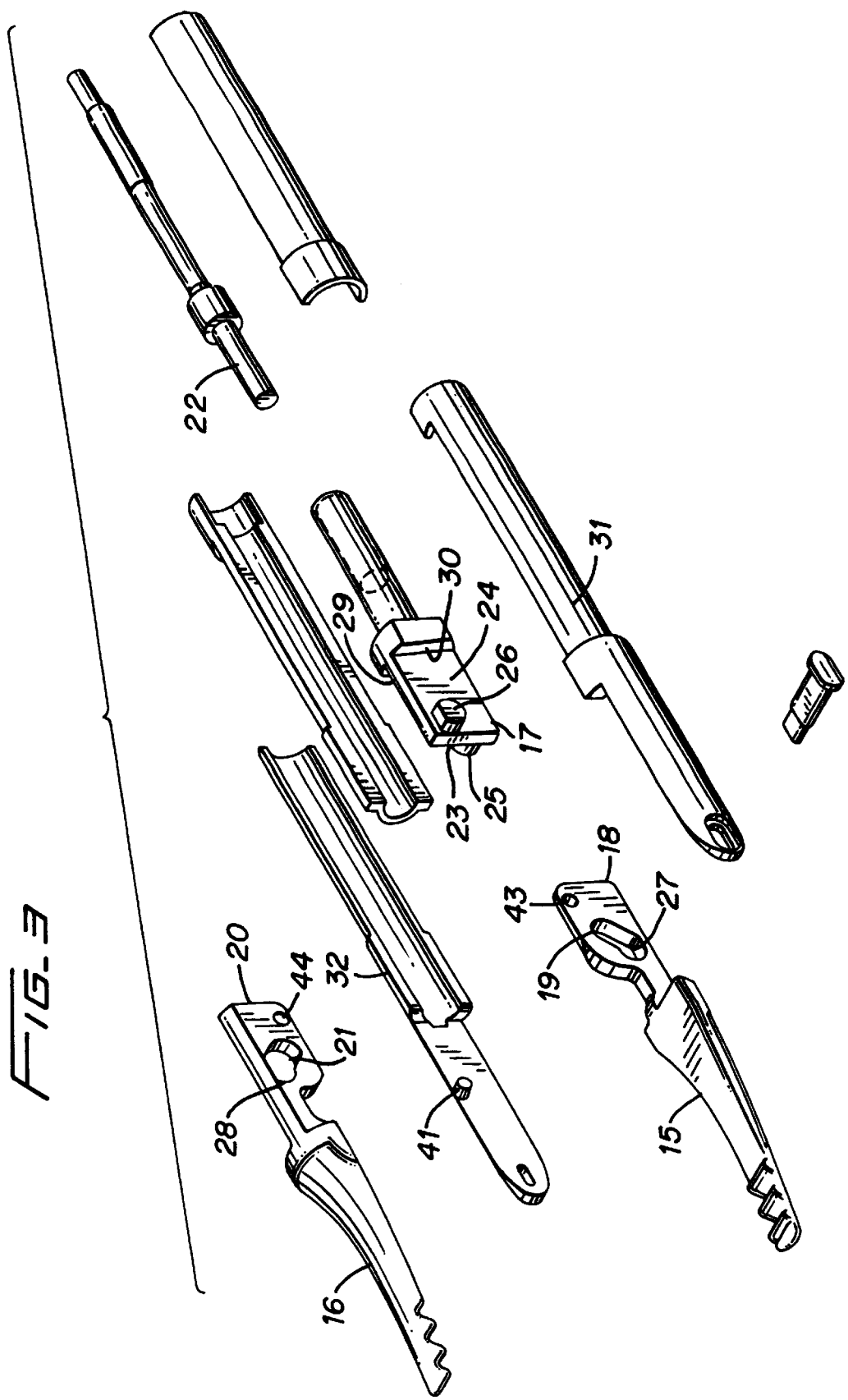
FIG. 3 is an exploded view of the distal end shown in FIG. 2.

Pieces that comprise the distal end 12 of the instrument 10 are shown in an exploded view in FIG. 3. The first jaw 15 and the second jaw 16 are shown separated from a yoke 17. The first jaw 15 has a first flange 18 and a first slot 19 therewithin. The second jaw 16 has a second flange 20 and a second slot 21 therewithin. Each jaw 15 and 16 is preferably formed from a single piece of stainless steel or other electrically conductive material.

Referring again to FIG. 3, the yoke 17 is attached to a pushrod 22. The yoke 17 is preferably formed from an electrically insulative material such as plastic. A first side 23 of the yoke 17 faces the first flange 18. A second side 24 of the yoke 17 faces the second flange 20. When the yoke 17 is positioned between the flanges 18 and 20, the yoke 17 also acts to electrically insulate the first jaw 15 from the second jaw 16. In this manner, bipolar electrosurgical current can be conducted through tissue grasped by the jaws 15 and 16 without short circuiting between the flanges 18 and 20.

A first pin 25 is located on the first side 23 to movably engage with the first slot 19. Similarly, a second pin 26 is located on the second side 24 to movably engage with the second slot 21. Each pin and slot combination works as a cam-follower mechanical linkage. Motion of the pushrod 22 moves the yoke 17 causing pins 25 and 26 to slide within their respective slots 19 and 21. The slots 19 and 21 are angled with respect to the distal ends of the jaws 15 and 16 such that the jaws 15 and 16 move in an arcuate fashion toward and away from each other. The pins 25 and 26 are different from the pivots 41 and 42. The pins 25 and 26 provide a force against the walls of the slots 19 and 21, creating a moment about the pivots 41 and 42.

The slots 19 and 21 are arranged such that distal motion of the pushrod 22 causes the jaws 15 and 16 to move together. Distal motion of the pushrod 22 is defined as motion in the direction of the distal end 12 of the instrument 10. Once the jaws 15 and 16 are closed together, the present invention holds the jaws 15 and 16 together with a compressive force on the pushrod 22.

One of the advantages of this invention is that shear forces on the pins 25 and 26 can be offloaded to prevent mechanical failure when large forces are being transmitted to the jaws 15 and 16. Each slot 19 and 20 has a cul-de-sac 27 and 28, respectively, as shown in FIG. 3. The first cul-de-sac 27 is an enlargement of the first slot 19 near its distal end. The second cul-de-sac 28 is an enlargement of the second slot 21 near its distal end. The cam-follower motion of the pins 25 and 26 in the slots 19 and 21 will bring the pins 25 and 26 into their respective cul-de-sac 27 and 28. This position of the pins 25 and 26 leaves a very small moment arm between the pins 25 and 26 and the pivots 41 and 42. The yoke 17 has shoulders 29 and 30 that can provide a relatively large moment about the pivots 41 and 42 to effect a high closure force between the jaws 15 and 16 without a high shear forces on the pins 25 and 26, as described below.

Once the pins 25 and 26 are in the cul-de-sacs 27 and 28, the force from the yoke is transmitted to the flanges 18 and 20 by a first shoulder 29 and a second shoulder 30. The shoulders 29 and 30 abut the proximal end of the flanges 18 and 20 to cause the jaws 15 and 16 to close together. The pivots 41 and 42 are preferably made of metal and can withstand relatively high shear forces. In contrast, pins 25 and 26 are preferably made of plastic and will break under relatively high shear forces. Thus, the shoulders 29 and 30 provide a moment lo about the pivots 41 and 42, thereby avoiding the necessity of applying high shear forces to the pins 25 and 26 when the moment arm from the pins 25 and 26 would be small. There is an angle a at which the pins 25 and 26 enter their respective cul-de-sacs 27 and 28 and the shoulders 29 and 30 abut the flanges 18 and 20. The angle α at which the forgoing occurs is preferably around three degrees.

The bipolar electrosurgical instrument 10 has first and second poles of alternating potential that are conducted along the instrument 10 and through tissue that is grasped between the jaws 15 and 16. The first pole is conducted from the proximal end 11 toward the distal end 12 along the pushrod 22. The second pole is conducted from the proximal end 11 toward the distal end 12 along the tube 13. The outer surface of the tube 13 is preferably coated with an electrically insulative material. There is also preferably an electrically insulative barrier between the pushrod 22 and the tube 13 to prevent short circuits in the instrument 10.

Figure 6:
FIG. 6 is a side views of an electrical spring contact.
Figure 7:
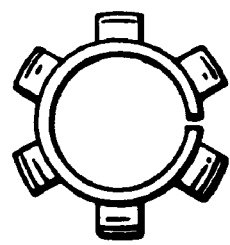
FIG. 7 is a front view of the spring contact shown in FIG. 6.

In the preferred embodiment, the distal end of the instrument 10 comprises an inner nose piece 31 and an outer nose piece 32, as shown in FIG. 2. The inner nose piece 3 1 is electrically connected with the pushrod 22, while the outer nose piece is electrically connected with the tube 13. The inner nose piece 31 and the outer nose piece 32 capture the yoke 17, along with the first and second flanges 18 and 20, as shown in FIG. 2. The yoke 17 moves axially, along an axis defined by the tube, in a space between the inner and outer nose pieces 31 and 32. A spacer stake 33 maintains the separation of the nose pieces 31 and 32 at their distal ends. The nose pieces 31 and 32 provide lateral support for the flanges 18 and 20 to help ensure that the pins 25 and 26 remain within the slots 19 and 21. The preferred embodiment also comprises an inner insulator 34 and an outer insulator 35 for maintaining electrical insulation between the poles. The outer insulator 35 is seated between the tube 13 and the inner nose 31, as shown in FIGS. 2 and 4. The inner insulator 34 is seated between the tube 13 and the pushrod 22. In this manner, the outer nose piece 32 can provide electrical continuity between the tube 13 and the second jaw 16, while the inner nose piece 34 can provide electrical continuity between the pushrod 22 and the first jaw 15. Since the pushrod Z " is slidably mounted within the tube 13, the preferred embodiment has a spring contact 36, as shown in FIGS. 6 and 7, mounted on the pushrod 22 to maintain an electrical connection with the inner nose piece 34 during axial motion.

The first and second jaws 15 and 16 each have ridges 37 and 38 at their distal ends that preferably nest together. The jaws 15 and 16 also have seal surfaces 39 and 40, as shown in FIG. 2. The width of the seal surfaces 39 and 40 is a parameter that affects the quality of the surgical outcome. The closure force between the jaws 15 and 16 varies along the length of the seal surfaces 39 and 40, with the largest force at the distal tip and the smallest force at the proximal end of the seal surfaces 39 and 40. It has been found through experimentation that good vessel sealing results are obtained when the closure force in grams divided by the width in millimeters is in the range of 400 to 650. Since the closure force varies with the length of the seal surfaces 39 and 40, it has been found to be advantageous to taper the width of the seal surfaces 39 and 40 along their length, with the widest width at the proximal end and the narrowest width at the distal end. This design allows the jaws 15 and 16 to apply a relatively constant closure force per unit width, preferably 525 grams per millimeter width.

A method of making a laparoscopic bipolar electrosurgical instrument 10 is also herein described. The method comprises the step of forming a first jaw 15 having a first flange 18 with a first slot 19, and a second jaw 16 having a second flange 20 with a second slot 21. The jaws 15 and 16 are preferably formed in a casting process, although it is also possible to machine the jaws 15 and 16 from stock. The casting process may include injecting powdered metal under pressure into a mold, and then applying heat.

Other steps in the method include attaching a yoke 17 to a pushrod 22, and electrically insulating the first flange 18 from the second flange 20 with the yoke 17. The yoke 17 is preferably an injection molded plastic part with features including a first shoulder 29 and a second shoulder 30.

During assembly of the distal portion of the instrument 10, steps in the method include engaging a first pin 5 with the first slot 19, and engaging a second pin 26 with the second slot 21. The slots 19 and 21 are shaped such that a subtended angle a between the first and second jaws 15 and 16 decreases with distal motion of the pushrod 17, and the slots 19 and 20 are formed with cul-de-sacs 27 and 28 positioned to relieve shear stresses on the first and second pins 25 and 26 at the subtended angle $\alpha$ approximately wherein the first and second shoulders 29 and 30 engage the first and second flanges 18 and 20.

Further steps in the method comprise: surrounding at least a portion of the pushrod 22 with an electrically conductive tube 13; electrically insulating the tube 13 from the pushrod 22; electrically connecting an inner nose piece 31 to the pushrod 22, and electrically connecting an outer nose piece 32 to the tube 13, wherein the inner nose piece 31 and the outer nose piece 32 capture the yoke 17 along with the first and second flanges 18 and 20 to conduct bipolar electrosurgical current to the first and second jaws 15 and 16. In the preferred embodiment, there is a step of electrically connecting the pushrod 22 and the inner nose piece 31 with a spring contact 36.

The method of making the instrument 10, in some embodiments, includes the steps of tapering the width of the seal surfaces 39 and 40 along the length of each of the first and second jaws 15 and 16.

While a particular preferred embodiment has been illustrated and described, the scope of protection sought is in the claims that follow.

What is claimed is:

1. A laparoscopic bipolar endoscopic instrument, comprising:

first and second jaw members, one of the jaw members being movable relative to the other of the jaw members from a first open position wherein the jaw members are disposed in spaced relation relative to one another to a second clamping position wherein the jaw members cooperate to grasp tissue therebetween, an electrically conductive push rod for connecting the first jaw member to a first electrical potential and an electrically conductive tube for connecting the second jaw member to a second electrical potential such that the jaw members are capable of conducting bipolar energy through the tissue held therebetween;

a yoke having at least one pin attached thereto which slidably engages the law members, the yoke being movable such that the pin imparts movement of the jaw members from the first and second positions;

a pair of shoulder portions attached to the yoke which are configured to abut the jaw members when the jaw members are moved into the second position to relieve shear stress on the pin during clamping and sealing of the tissue; and a handle which cooperates with the push rod for imparting movement to the yoke.

2. The laparoscopic bipolar electrosurgical instrument of claim 1 wherein the electrically conductive tube surrounds at least a portion of the pushrod, and an electrically insulative layer is disposed between the tube and the pushrod capable of supporting an electrosurgical alternating potential across the tube and the pushrod.

3. The laparoscopic bipolar electrosurgical instrument of claim 2 further comprising:

an inner nose piece electrically connected to the pushrod, and an outer nose piece electrically connected to the tube, wherein the inner nose piece and the outer nose piece capture the yoke to conduct bipolar electrosurgical current to the first and second jaw members.

4. The laparoscopic bipolar electrosurgical instrument of claim 3 further comprising an electrical spring contact between the pushrod and the inner nose piece to provide electrical continuity therebetween.

5. The laparoscopic bipolar electrosurgical instrument of claim 1 further comprising ridges in each of the first and second jaw members.

6. The laparoscopic bipolar electrosurgical instrument of claim 1 wherein each of the first and second jaw members has a seal surface with width and a length, and wherein at least one location along the length has a width such that the closure force in grams divided by the width in millimeters is in the range of 400 to 650.

7. The laparoscopic bipolar electrosurgical instrument of claim 6 wherein the width of at least one of the seal surfaces is tapered along its respective length.

8. The laparoscopic bipolar electrosurgical instrument of claim 7 wherein the closure force in grams divided by the width in millimeters is approximately constant along the length for each of the first and second jaw members.

* * * * *